(12) United States Patent
Chaton et al.

(10) Patent No.: US 7,718,422 B2
(45) Date of Patent: May 18, 2010

(54) DEVICE FOR ENHANCING BROAD BAND FLUORESCENCE WITH LOW LOSS AND BIOLOGICAL OR CHEMICAL OPTIC SENSOR USING THE SAME

(75) Inventors: Patrick Chaton, Theys (FR); Françoise Vinet, Grenoble (FR); Pierre Barritault, Grenoble (FR); Stéphane Getin, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 773 days.

(21) Appl. No.: 10/450,100

(22) PCT Filed: Dec. 12, 2001

(86) PCT No.: PCT/FR01/03960
§ 371 (c)(1),
(2), (4) Date: Dec. 29, 2003

(87) PCT Pub. No.: WO02/48691
PCT Pub. Date: Jun. 20, 2002

(65) Prior Publication Data
US 2004/0092028 A1     May 13, 2004

(30) Foreign Application Priority Data
Dec. 14, 2000    (FR) .................................. 00 16317

(51) Int. Cl.
*G01N 33/551* (2006.01)
(52) U.S. Cl. ............... 435/288.7; 385/129; 385/130; 385/131; 422/82.05; 422/82.08; 422/82.11; 435/808; 436/524

(58) Field of Classification Search .............. None
See application file for complete search history.

(56) References Cited

U.S. PATENT DOCUMENTS
3,979,184 A * 9/1976 Giaever ............ 422/57
(Continued)

FOREIGN PATENT DOCUMENTS
DE      29 46 234 A1    5/1981
WO      9403774 A1      2/1994

OTHER PUBLICATIONS
Sadafumi, Yoshida, et al., "Optical thin films and devices", Japan, University of Tokyo Press, Sep. 20, 1994, first printing, pp. 156-157.
Office Action dated Jun. 21, 2007, JP 2002-549949 (corresponding application).

*Primary Examiner*—Christopher L Chin
(74) *Attorney, Agent, or Firm*—Nixon Peabody LLP

(57) ABSTRACT

The invention concerns a device for enhancing fluorescence comprising a support (10) carrying fluorescence enhancement means (11), the fluorescence enhancement means offering a reception surface for chemical or biological elements intended to be read by detection of a fluorescence signal emitted by a fluorophore, associated with the chemical or biological elements, under the effect of an excitation light beam. The fluorescence enhancement means (11) is made up of a thin, transparent, dielectric layer or a stack of thin, transparent, dielectric layers (12 to 16) ensuring a mirror function for the fluorescence signal and excitation light beam, the material of the thin layer or of each thin layer of the stack being chosen from among the following materials: $TiO_2$, $Ta_2O_5$, $HfO_2$, $ZrO_2$, $MgO$, $SiO_2$, $Si_3N_4$, $MgF_2$ and $YF_3$. The fluorescence enhancement device may be used for a biological or chemical optic sensor.

5 Claims, 1 Drawing Sheet

U.S. PATENT DOCUMENTS

| | | | |
|---|---|---|---|
| 4,820,649 A * | 4/1989 | Kawaguchi et al. | 436/501 |
| 5,242,828 A * | 9/1993 | Bergstrom et al. | 435/287.1 |
| 5,418,136 A | 5/1995 | Miller et al. | |
| 5,468,606 A | 11/1995 | Bogart et al. | |
| 5,478,755 A | 12/1995 | Attridge et al. | |
| 5,482,830 A | 1/1996 | Bogart et al. | |
| 5,541,057 A | 7/1996 | Bogart et al. | |
| 5,550,063 A | 8/1996 | Bogart | |
| 5,552,272 A | 9/1996 | Bogart | |
| 5,629,214 A | 5/1997 | Crosby | |
| 5,639,671 A | 6/1997 | Bogart et al. | |
| 5,869,272 A | 2/1999 | Bogart et al. | |
| 5,955,377 A | 9/1999 | Maul et al. | |
| 6,060,237 A | 5/2000 | Nygren et al. | |
| 6,355,429 B1 | 3/2002 | Nygren et al. | |
| 6,783,938 B2 | 8/2004 | Nygren et al. | |
| 6,867,900 B2 | 3/2005 | Weisbuch et al. | |

\* cited by examiner

DEVICE FOR ENHANCING BROAD BAND FLUORESCENCE WITH LOW LOSS AND BIOLOGICAL OR CHEMICAL OPTIC SENSOR USING THE SAME

CROSS-REFERENCE TO RELATED APPLICATION

This application claims priority based on International Patent Application No. PCT/FR01/03960, entitled "Device for Enhancing Broadband Fluorescence with Low Loss and Biological or Chemical Optic Sensor Using the Same" by Patrick Chaton, Francoise Vinet, Pierre Barritault and Stephane Getin, which claims priority of French application no. 00/16317, filed on Dec. 14, 2000, and which was not published in English.

CROSS-REFERENCE TO SEQUENCE LISTING

The sequence listing included in the electronic file submitted herewith via EFS-Web as one of the parts of this application entitled "434299-521 Sequence Listing.txt" is incorporated by reference into this application in its entirety.

TECHNICAL FIELD

The invention concerns a device for enhancing broadband fluorescence with low loss. It also concerns a biological or chemical optic sensor using said fluorescence enhancement device.

PRIOR ART

The detection of chemical or biological reactions on a solid support by fluorescent labelling is made difficult by the low signal levels emitted by the fluorophores.

Two methods exist for enhancing the signal emitted by fluorophores. These are based on exacerbation of the exciter field by evanescent waves. These methods imply the use of dedicated scanners. On account of their guided mode operating principles, these methods are not broadband. Excitation must be conducted under a well-determined condition of resonance.

The document "Sensitivity enhancement of optical immunosensors by the use of a surface plasmon resonance fluoroimmunoassay" by F. W. ATTRIDGE et al., Biosensors and Bioelectronics, vol. 6, 1991, page 201 to 214, discloses a method for enhancing fluorescence based on surface plasmons. This method consists of depositing on the biosensor, between the substrate and the layer containing the chemical or biological elements, a thin metal layer (of silver for example) coated with a layer of silica. The biosensor is placed on a hemispherical lens (or a prism). The excitation beam passes through this component and arrives on the silver layer in such manner that surface plasmons are generated. This phenomenon sets up an intense excitation field making it possible to exacerbate fluorescence emission. Unfortunately, the use of a thin metal layer implies the existence of nonradiative losses detrimental to fluorescence enhancement.

The document "Slab waveguides in Chemistry" by L. KANG et al., Critical Reviews in Analytical Chemistry, vol. 21, NO 6, 1990, pages 377 to 388, discloses a method for enhancing fluorescence based on guided optics. This method consists of depositing a guiding structure on the biosensor, between the substrate and the layer containing the chemical or biological elements. By means of an appropriate coupling device (prism, network) the light is injected into the guide. The reflection of the guided light at the guide/fluorophore-containing medium interface forms an evanescent wave in the medium containing the fluorophores. This evanescent wave creates overintensity so that excitation of the fluorophore is such that it emits a substantial quantity of light.

With these two methods, it is therefore possible to increase the fluorescence signal. However, as mentioned above, these methods imply the use of scanners. These methods are not broadband.

SUMMARY OF THE INVENTION

The objective of the invention is to enhance fluorescence using conventional (propagating) waves, which enable reading of the fluorescence signal by commercially available instruments. It also sets out to enlarge the possibilities of fluorescence enhancement using a component operating on a wide spectrum band. Finally its concerns limiting nonradiative losses due to imperfections of the materials used.

The detection method put forward by the invention is based on the depositing of a stack of thin optic layers which perform a mirror function with low non-radiative losses.

A first subject of the invention is a device for enhancing fluorescence comprising a support carrying fluorescence enhancement means, the fluorescence enhancement means offering a reception surface for the chemical or biological elements intended to be read by detection of a fluorescence signal emitted by a fluorophore, associated with the chemical or biological elements, under the effect of an excitation light beam, characterized in that the fluorescence enhancement means is made up of a thin, transparent, dielectric layer or a stack of thin, transparent, dielectric layers ensuring a mirror function for the fluorescence signal and for the excitation light beam, the material of the thin layer or of each thin layer of the stack being chosen from among the following materials: $TiO_2$, $Ta_2O_5$, $HfO_2$, $ZrO_2$, $MgO$, $SiO_2$, $Si_3N_4$, $MgF_2$ and $YF_3$.

The thickness e of the thin layer or the thickness of each thin layer of the stack may be calculated using the following equation:

$$N \cdot e = k \cdot \lambda / 4$$

where N is the refractive index of the material of the thin layer for length $\lambda$ of the reading signal and k is an uneven whole number.

Optionally, the fluorescence enhancement means is means deposited on a structured surface of the support.

Depending upon applications, said reception surface may be a surface offering hydroxyl functions or a surface offering aldehyde functions.

A second subject of the invention is a biological or chemical optic sensor formed by the above-described device, said reception surface carrying chemical or biological elements labelled with a fluorophore.

BRIEF DESCRIPTION OF THE DRAWINGS

The invention will be better understood and other advantages and particular aspects will become apparent on reading the following description, given as a non-restrictive illustration, accompanied by the appended drawings in which.

DETAILED DESCRIPTION OF EMBODIMENTS OF THE INVENTION

Figure 1:
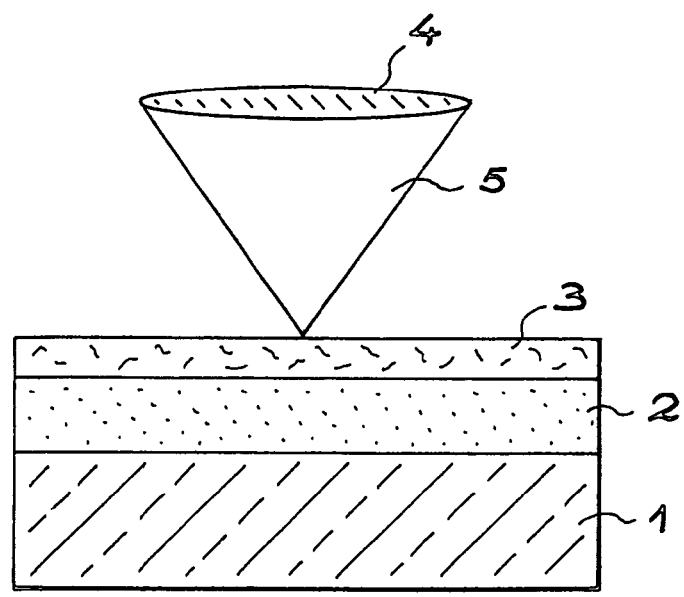
FIG. 1 is a cross-section view of an optic sensor according to the present invention

FIG. 1 is a cross-section view of a biological or chemical optic sensor according to the present invention. It shows a substrate 1 carrying fluorescence enhancement means 2 which in turn carries chemical or biological substances labelled with a fluorophore. These substances are shown in the form of a layer 3.

This figure shows a focusing lens 4 and a reading beam 5 to symbolise the reading and excitation system by epifluorescence microscope examination.

The fluorescence enhancement means 2 may be made up of a stack of thin dielectric layers. These thin layers may be formed of the following materials: $TiO_2$, $Ta_2O_5$, $HfO_2$, $ZrO_2$, $MgO$, $SiO_2$, $Si_3N_4$, $MgF_2$ and $YF_3$. These materials may be deposited using PVD-type techniques (electron gun, sputtering), CVD techniques or sol-gel depositing methods.

These fluorescence enhancement means in the form of thin layers may be deposited on the entirety of the substrate or on a structured substrate. In the latter case, they may be positioned using conventional lithography techniques, "lift-off" techniques or mechanical masking. At all events, the stoicheiometry of the materials must be fully controlled. Particular care must be given to the last layer to prevent the formation of nonradiative losses.

The last thin layer must have biological compatibility with the probes to be grafted onto this layer. Silica or silicon nitride have this quality of biological compatibility.

The fluorescence enhancement means ensures a mirror function for the excitation wave length. For this purpose, all that is required is that the optical thickness of the different thin layers complies with the following rule:

$$N \cdot e = k \cdot \frac{\lambda}{4} \quad (1)$$

N being the refractive index of the material under consideration at the excitation wavelength, k being an uneven whole number, $\lambda$ being the excitation wavelength and e the mechanical thickness of the layer under consideration. By "optical thickness" is meant the product of the refractive index with the mechanical thickness of the thin layer for the wavelength under consideration.

A description follows of the fabrication of a fluorescence enhancement device for a DNA biochip, this device being optimised for the CY3 fluorophore.

Figure 2:
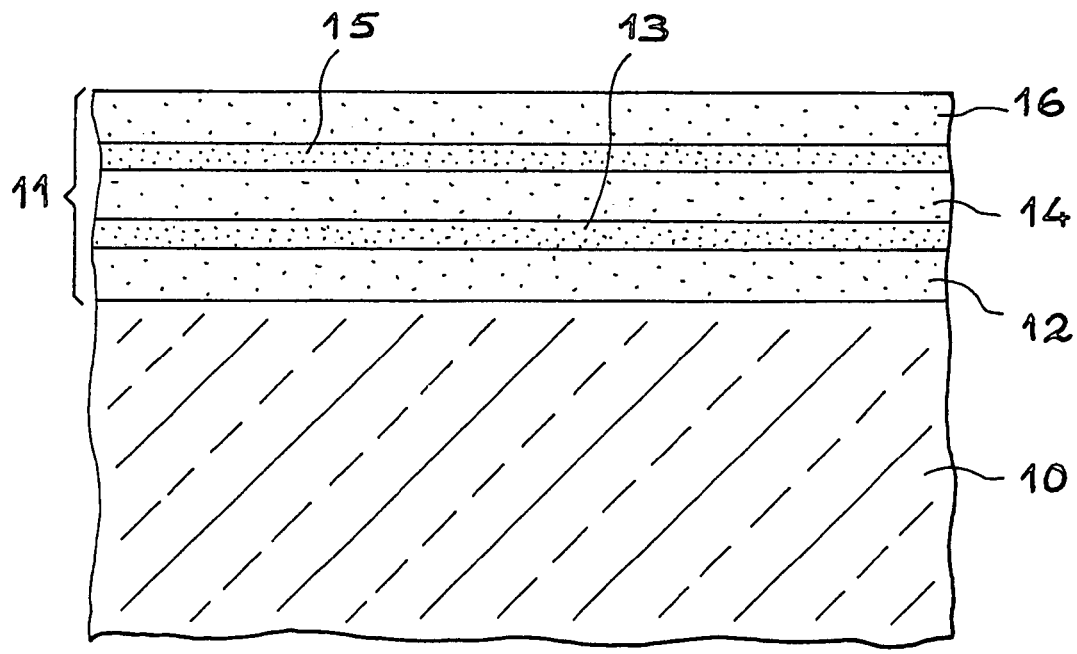
FIG. 2 is a cross-section view of a fluorescence enhancement device according to the present invention.

FIG. 2 is a cross-section view of such a device. On substrate 10 in silicon, the fluorescence enhancement means 11 has been deposited in the form of five layers referenced 12 to 16. This device is intended for an excitation wavelength of approximately 550 nm for the CY3 fluorophore.

Layers 12, 14 and 16 are in $SiO_2$, having a refractive index of 1.46 for the excitation wavelength under consideration. Layers 13 and 15 are in $Si_3N_4$, having a refractive index of 2 for the excitation wavelength under consideration.

By applying rule (1) above, for k=1 a mechanical thickness of 94 nm is obtained for each layer of $SiO_2$ and a mechanical thickness of 69 nm for each layer of $Si_3N_4$.

With this stack of layers, the available band width for excitation is ±100 nm around the centring wavelength of 550 nm. It is therefore compatible both with the CY3 fluorophore and the CY5 fluorophore.

For fluorescence reading, a CY3-optimised microscope can be used. It is fitted with an optic filter for selection of light excitation at 546 nm for a spectrum width of approximately 10 nm.

The layers of $SiO_2$ can be deposited using a method of CVD type at 800° C. The $Si_3N_4$ layers can be deposited using a CVD-type method at 730° C.

The fluorescence enhancement means may only comprise one layer, for example a layer of $SiO_2$ having a mechanical thickness of 500 nm.

A description follows of some grafting and hybridisation steps on the fluorescence enhancement device of the invention.

One first example concerns the in situ grafting of oligonucleotides. The free surface of the fluorescence enhancement means is treated by chemical route to obtain hydroxyl functions on the surface. The functionalised device is then placed in an automatic oligonucleotide synthesizer (Expedite 8909, PE Biosystems) with which an oligonucleotide with 20 units can be grown, base per base, having a sequence of 3' TTT TTA TCT CAC CCA AAT Ag5' (SEQ ID NO: 1).

A second example concerns the grafting of pre-synthesized oligonucleotides. The free surface of the fluorescence enhancement means is treated by chemical route to obtain an aldehyde function in this case. A solution of oligonucleotides (5 µM) containing an $NH_2$ function at 5' in a phosphate buffer is deposited on the substrate under conditions enabling the formation of an imine covalent bond (—CH=N—) between the device and the oligonucleotide. After overnight incubation at room temperature, the device is rinsed in a solution of SDS (sodium dodecylsulphate) then in water. The imine bond being rather unstable, a reduction step is provided for the double bond in the presence of $Na_2BH_4$ for 10 minutes. The device is again rinsed with SDS then in water. It is then dried in a stream of nitrogen.

The hybridisation step consists of placing the device containing the probes in the presence of a solution formed of a buffer and of targets having complementary sequences to the probes comprising a CY3 fluorophore at position 5'. The conditions of hybridisation enabling pairing of the probes and targets are as follows:

hybridisation solution: 300 µl of 0.2 µM targets +900 µl hybridisation buffer H-7140/Sigma.

incubation of the device covered with the solution in an oven at 40° C. for 1 hour, rinsing in a SSC 2× buffer bath (S-6639/Sigma) for 1 minute, rinsing in a SSC 0.2× buffer bath (S-6639/Sigma) for 1 minute, drying in a stream of nitrogen.

Observation under a fluorescence microscope (Olympus BX60) of the different stacks of the invention, leads to the following fluorescence intensities for integration times of 1 second with a 5× lens (units are expressed in arbitrary units AU):

support in Si and monolayer of $SiO_2$ with a thickness of 500 nm deposited by decomposition of tetraethoxysilane (TEOS), in situ synthesis: 225 AU.

support in Si and stack of $SiO_2$ and $Si_3N_4$ layers, in situ synthesis: 593 AU. For this type of grafting, the same ratio of fluorescence enhancement is obtained with a target concentration that is 4 times weaker (0.05 µM instead of 0.2 µM), Support in Si and monolayer of $SiO_2$ with a thickness of 500 nm deposited by decomposition of TEOS, pre-synthesized oligonucleotides: 140 AU, Support in Si and stack of $SiO_2$ and $Si_3N_4$ layers, pre-synthesized oligonucleotides: 326 AU.

It is to be noted that the invention also applies to reading systems of confocal scanning type.

The stack of thin, optic dielectric layers allows verification of several points.

It is possible to increase the excitation field of the fluorophores relative to a configuration without a stack of thin layers. This makes it possible to increase the quantity of light emitted by the fluorophores. The simplest solution consists of depositing a stack of quarter-wave type.

It is possible to improve the directionality of the light emitted by the fluorophores. This brings improvement in the quantity of light collected by the microscope or reading scanner. This is not the case with devices of the prior art.

The use of this stacking, which can be compared to a "one-dimensional photonic crystal" has forbidden band properties giving it a wide spectral excitation domain. The excitation wavelength may be chosen from the entirety of the bandwidth of the dielectric mirror (typically >100 nm). In addition, this also enables the simultaneous use of several fluorophores compatible with this spectral band. This is not the case with devices of the prior art.

The preceding property also provides flexibility in the choice of incidence of the excitation light. This is not the case with devices of the prior art.

It is possible to obtain signal enhancement working under normal incidence, in the free space, without having recourse to guide structures. In this case, excitation of the biosensor fluorophores can be made using a non-dedicated system. The invention is compatible with commercially available apparatus.

With the invention, it is possible to block the excitation light in the stack and to limit parasite fluorescence coming from the substrate.

With the invention, it is also possible not to use thin metal layers in the stack. The presence of these materials causes the onset of nonradiative losses which limit the efficiency of fluorescence enhancement.

The invention proposes stacks with high optical quality in terms of losses through absorption. In particular, it is sought to minimise the influence of the last thin layer (the one on which the fluorophores are deposited). This layer is especially optimised. It is sought to obtain the lowest possible extinction coefficients (imaginary index). Typically, extinction coefficients of less than $10^{-3}$ are required. In this case, nonradiative losses are limited.

---

---

The invention claimed is:

1. A fluorescence enhancement device comprising a support for carrying fluorescence enhancement means, the fluorescence enhancement means providing a reception surface for chemical or biological elements readable by detection of a fluorescence signal emitted by a fluorophore, associated with the chemical or biological elements, under the effect of an excitation light beam, in which the fluorescence enhancement means is made up of a stack of thin, transparent, dielectric layers providing a mirror function with low, non-radiative losses, allowing an increase of the excitation field of the fluorophore and an increase in the quantity of light emitted thereby and an increase of the fluorescence signal, and a limit of parasitic fluorescence from the substrate, the material of each thin layer of the stack being selected from among the following materials: $TiO_2$, $Ta_2O_5$, $HfO_2$, $ZrO_2$, MgO, $SiO_2$, $Si_3N_4$, $MgF_2$ and $YF_3$, in which a thickness e of each thin layer of the stack is determined in accordance with the following equation:

$$N \cdot e = k \cdot \lambda / 4$$

where N is the refractive index of the material of the thin layer for wavelength λ of the reading signal and k is an uneven whole number, a free surface of the last thin film of the stack being biologically compatible with probes to be grafted in order to constitute said reception surface.

2. The device according to claim 1, in which the fluorescence enhancement means is means deposited on a structured surface of the support.

3. The device according to claim 1, characterized in that said reception surface is a surface offering hydroxyl functions.

4. The device according to claim 1, in which said reception surface is a surface offering aldehyde functions.

5. A device according to claim 1, said reception surface carrying chemical or biological elements labelled with a fluorophore.

* * * * *

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: oligonucleotide

<400> SEQUENCE: 1
tttttatctc acccaaatag                                                20